United States Patent [19]

Michael et al.

[11] Patent Number: 4,469,677
[45] Date of Patent: * Sep. 4, 1984

[54] POLYPEPTIDE ACTIVE IMMUNOSUPPRESSANT FRACTION

[76] Inventors: J. Gabriel Michael, 418 Chisholm Trail, Cincinnati, Ohio 45215; Amadeo J. Pesce, 5769 Whitechapel, Cincinnati, Ohio 45236

[ * ] Notice: The portion of the term of this patent subsequent to Jul. 6, 1999 has been disclaimed.

[21] Appl. No.: 393,771

[22] Filed: Jun. 30, 1982

Related U.S. Application Data

[63] Continuation-in-part of Ser. No. 139,881, Feb. 19, 1980, Pat. No. 4,338,297.

[51] Int. Cl.$^3$ ............... A61K 39/36; A61K 39/35; C07G 7/00
[52] U.S. Cl. ................. 424/91; 260/112 R; 424/88
[58] Field of Search ............. 424/91, 88; 260/112 R

[56] References Cited

U.S. PATENT DOCUMENTS 4,158,705  6/1979  Malley ........................... 424/91

OTHER PUBLICATIONS

Chemical Abstracts, vol. 93, p. 702, Abst. No. 68349w, 1980.
Chemical Abstracts, vol. 91, p. 489, Abst. No. 173156n, 1979.
Chemical Abstracts, vol. 93, p. 477, Abst. No. 184103k, 1980.
King, T. P., Advan. Immunol., vol. 23, p. 77, 84, 87, 88, 89, 91, 91, 1976.

*Primary Examiner*—Blondel Hazel
*Attorney, Agent, or Firm*—Frost & Jacobs

[57] ABSTRACT

Immunosuppressive polypeptide fractions prepared by enzymatic digestion of specific allergens are non-reactive in animals and humans and effective by parenteral administration, the immunosuppression being antigen specific, affecting production of immunoglobulins. A method of producing immunosuppressive polypeptide fractions and a method of desensitizing mammals therewith are disclosed.

13 Claims, No Drawings

POLYPEPTIDE ACTIVE IMMUNOSUPPRESSANT FRACTION

CROSS REFERENCE TO RELATED APPLICATION

This application is a continuation-in-part of application Ser. No. 139,881, filed Feb. 19, 1980 now U.S. Pat. No. 4,338,297, in the names of the same inventors.

BACKGROUND OF THE INVENTION

Numerous polypeptide molecules cause an allergic reaction in man and animals. Hay fever, more particularly ragweed sensitivity, characterized classically by itching of the mucosa of the nose, mouth, pharynx and eyes, lacrimation, sneezing, watery nasal discharge, coughing and sometimes asthmatic wheezing afflicts a considerable number of humans. Sensitivity to bee venom is characterized classically by a wheal and flare reaction, swelling, anaphylaxis and occasionally death. Food allergies classically are manifested by urticaria, perhaps nausea, diarrhea, and hives.

It is known that the appearance of allergy or atopy is involved with production of a tissue-sensitizing immunoglobulin (IgE) antibody. These IgE antibodies have an affinity for receptors on cells in various body tissues. The receptors on mast cells and basophils are of special significance since these cells contain pharmacologically-active mediators, such as histamine, serotonin, and kinins concentrated in cytoplasmic granules. When IgE antibodies are fixed to mast cells and basophils, contact with antigens can result in cross-linking. This cross-linking causes degranulation of mast cells and basophils which in turn release the pharmacologically active mediators (particularly histamine) and which are responsible for manifestations of the allergic response.

Thus, these disturbances are caused by immunoglobulin E reacting with specific polypeptide molecules in these substances. Untreated, these disturbances can lead to asthma in the case of hayfever, disabling reactions in the case of insect venom and limited dietary intake in the case of foods. Treatment for hayfever usually entails trial of orally active antihistamines, sometimes in combination with sympathomimettes such as phenylpropanolamine or phenylephrine. The symptoms may thus be partially suppressed, but the basic physiological difficulty, the histamine release by the antibody antigen reaction, persists. Treatment of insect stings by these agents is not practical since it is not possible to know when the event may occur and the reaction can be very severe if treatment is not immediate. Similarly the food reaction must have immediate treatment to achieve its effect. Commonly these treatments are inadequate or unsatisfactory and resort must be had to a more fundamental treatment, particularly for the pollen and venom allergies, namely desensitization.

One of the conventional and widely used methods of treating allergy is by immunizing or desensitizing a patient by repeated injections of small, gradually increasing amount of antigen, which is believed to increase the levels of blocking immunoglobulin G (IgG) antibodies and at the same time to arrest the production of IgE antibodies. This apparently conflicting effect of antigen administration is not fully understood but apparently involves differences in immunoregulation of two different classes of antibodies, viz. IgG and IgE.

This desensitization is undertaken with extreme caution. Commencing with a very dilute preparation of ragweed allergen or bee venom allergen, injected subcutaneously, if there is no local reaction within an hour of injection, the next dose is doubled and administered in 3 or 4 days. To be used in the event of an anaphylactic reaction, there must be available for emergency administration, adrenaline, antihistamines and intravenously administrable antiinflammatory corticosteroids during the testing and desensitization procedures. Both the time and precautions accompanying the conventional ragweed desensitization procedures are inconvenient. Benefits obtained by such treatments are frequently inconsistent.

This invention is concerned with the discovery, manufacture and method of use of a new and specific polypeptide immunosuppressant fraction produced by controlled proteolytic digestion of a polypeptide allergen which, upon administration for the specific allergic reaction in mammals, including humans, effects protection against said allergens without the accompanying and dangerous possibility of anaphylactic shock and other disadvantages indicated above. Pollen allergen preparations of this invention are made, illustratively, from common ragweed, giant ragweed, rye (Groups I, II and III), June grass, orchard grass, sweet vernal grass, red top, timothy, yellow dock, wheat, corn, sagebrush, blue grass, California annual grass, pig weed, Bermuda grass, Russian thistle, mountain cedar, oak, box elder, sycamore, maple, elm, etc. Ragweed constitutes the most prevalent and noxious of these and is the primary example illustrated herein. However, the pollen allergens of grasses and trees are chemically similar to ragweed pollen, the major alergens being acidic proteins of varying molecular weights within the range of about 20,000 to 40,000, as described by T. P. King, *Advances In Immunology,* 77-105, 1976, Academic Press, New York, N.Y. This publication further characterizes bee venom allergens (principally phospholipase and hyaluronidase) and food allergens (e.g. ovalbumin and ovomucoid) as being similar to the inhalant allergens, all being globular proteins.

According to King antigen E of short ragweed pollen comprises two non-identical polypeptide chains held together in the native molecule by noncovalent forces, the chains having molecular weights of about 26,000 and 13,000 daltons, respectively. Ovalbumin is reported as having a molecular weight of 44,000, while ovamucoid is a glycoprotein having a molecular weight of about 27,000. Bee venom phospholipase has a molecular weight of about 15,800, and hyaluronidase has a molecular weight of about 50,000. Both are basic glycoproteins.

King further reports that ragweed pollen antigen E is stable toward proteolytic digestion at neutral pH by trypsin, chymotrypsin and papain, but is digested by nagarase at neutral pH. Nagarase-digested antigen E showed less than 0.001% of the allergenic activity of intact antigen E. Ryegrass allergens Groups I and II are readily digested by trypsin and chymotrypsin, with complete removal of the antigenic and allergenic activities as well as haptenlike inhibitory activity, in the case of Group I.

The purpose of the proteolytic digestion reported by King was to show that allergens were polypeptides. The products of digestion described by King exhibited entirely different properties from those of the present invention.

As a general observation King states:

"The dominant antigenic determinants of the major allergens of ragweed and ryegrass pollens, codfish, and bee venom are dependent on both the primary structure and the conformation of the molecule, a property in common with the other globular protein antigens."

An article by L. Berrens, *Annuals New York Academy of Sciences,* 221: 183-198, 1974, attributes allergenic activity to lysine-sugar Amadori products which were present in all the allergens examined by him, based on the following observations: "Mild oxidation of these atopic allergens, using alkaline potassium ferric cyanide, hydrogen peroxide, or ultraviolet radiation, which selectively destroyed the highly vulnerable 1-amino-1-deoxy-2 ketose side chains, caused allergenic activity to diminish, without serious damage to the *antigenic* integrity of the carrier molecule.

The synthetic introduction of (lysine)-sugar structures of the above configuration into inactive carrier proteins led to the production of allergenically active preparations, featuring all the characteristic chemical properties of 'natural' allergens.

In the light of these results, we have gradually come to regard the 'lysine-sugar' site as essential in priming the allergic reaction."

Insect venom allergen preparations of this invention are made, illustratively, from bee venom, yellow jacket venom and other insects of the Hymenoptera order.

Food allergen preparations of this invention are made from egg, milk, and other sources of similar allergenic proteins.

The process of the present invention, involving controlled proteolytic enzyme digestion, is operable with all allergens of the above types of which applicants are aware. The polypeptide active immunosuppressant fractions of this invention, in contrast to prior art allergens, can be administered without likelihood of anaphylaxis.

Attempts to achieve separation of protective and allergic inducing activities for the treatment of pollen sensitivities, particularly in ragweed-sensitive individuals, have been reported. For example, Ishizaka, K., et al, *J. Immunol.* 113: 70-77, 1974, prepared four modification of the active allergenic fraction of ragweed pollen extract, antigen E, namely urea denatured antigen E (UD), its alpha and beta polypeptide chains and a reduced carboxymethylated antigen E (RC). All modifications lost antigenic determinants present in the unmodified antigen E and accordingly could not be used to achieve satisfactory antibody production against antigen E in humans. Each of the four preparations failed to combine with human gamma globulin, human IgG, against the original native antigen, and did not induce erythema wheal reactions in ragweed sensitive individuals. Since modified antigens do not induce allergenic reactions in the patients but are capable of stimulating T cells, carrier-specific helper cells, Ishizaka speculated that such modified antigens may change the T cell population without side effects. Subsequently, Ishizaka, et al., *J. Immunol.,* 114: 110-115, 1975, reported that test results collectively indicate that a major population of B cells stimulated by native antigen is different from the majority of B cells stimulated by the urea-modified antigen. Further work on UD or the alpha-polypeptide chain isolated from the denatured molecule provided additional evidence that these materials prime T cells specific for native antigen E (Takatsu, et al., *J Immunol.,* 115: 1469-1476, 1975 and 116: 1257-1264, 1976). It must be recognized that the denatured protein and polypeptide chains obtained from the denatured protein themselves introduce foreign material which could aggravate allergic sensitivity by providing yet another foreign sensitizing material, over and above ragweed antigen, to which the body may react.

In addition to urea-denatured antigens described by Ishizaka et al, which do not react with antibodies to native antigen molecules, the literature has disclosed other modified antigen preparations. These may be summarized as follows:

Glutaraldehyde polymerized antigen: R. Patterson, *J. Allergy and Clinical Immunology,* 68: 85-90, 1981 immunogenic, but reactive and administrable only in small amounts.

Formaldehyde treated antigen: D. G. Marsh et al, *J. Allergy and Clinical Immunology,* 68: 449-459, 1981—non-reactive but ineffective in immunosuppression.

Antigen conjugated with d-amino acids or polyethylene glycol: F. Liu et al, *Proc. National Academy of Sciences USA,* 76: 1430-1434, 1979; and A. H. Sehon et al, *J. Allergy and Clinical Immunology,* 64: 242-250, 1979—immunosuppressive, reactivity similar to unmodified antigenic extracts.

The art has thus failed to show or suggest the preparation of a pollen desensitizing agent free of anaphylactic reactivity, such as could be used therapeutically.

SUMMARY OF THE INVENTION

We have now found that a safe and effective pollen, venom, and food desensitizing material is preparable from pollen, venom, and food extracts treated with proteolytic enzyme inclusive of exopeptidases e.g. carboxypeptidase A, and endopeptidases, e.g. trypsin, chymotrypsin, papain, particularly, bacterial protease, nagarase, or pepsin, and preferably then detoxified by molecular exclusion chromatography, molecular filtration or affinity absorption to remove fractions exacerbating the allergy to be treated, to produce a product which possesses ability to suppress the immune response to said antigens, thereby avoiding dangers normally associated with attempted desensitization by use of said antigens. The polypeptide allergen desensitizing product is obtained by proteolytic digestion of the primary allergen to produce an antigen-specific polypeptide fraction apparently having only one functional antigenic valence on each molecule, thereby not participating in reactions involving antigen bridging, including antibody formation and anaphylactic response. The polypeptide fraction has a molecular weight of less than 10,000. The product of this invention does not give a positive wheal and flare reaction in sensitive individuals, nor will it react in the passive cutaneous anaphylaxis reaction (PCA) in rats sensitized by specific illustratum with ragweed antigen, bee venom antigen or egg white ovalbumin antigen. These polypeptide fragments have been found effective in suppressing immune response by activating T suppressor cells and/or inactivating B cells.

According to the invention there is thus provided an allergen desensitizing polypeptide fraction derived by proteolytic enzymatic digestion from a specific allergen causing the allergic reaction to be treated, said fraction consisting essentially of a degraded polypeptide having a molecular weight of less than about 10,000, a nominal molecular radius not greater than about 15 angstroms, an inability to precipitate with specific antibodies, an inability to induce substantial passive cutaneous anaphylaxis reaction in a sensitized mammal, an inability to release histamine from sensitized mast cells or basophils, an inability to induce substantial antibody response, a capability of significantly inhibiting immunological reactions between a whole allergen and its antibody, and a capability of inducing antigen-specific suppression.

The invention further provides a method of producing an allergen desensitizing polypeptide fraction which comprises subjecting an aqueous extract of a native allergen to digestion by a proteolytic enzyme and obtaining a reaction product consisting essentially of a degraded polypeptide fraction having a molecular weight of less than about 10,000 and a nominal molecular radius not greater than about 15 angstroms.

A method of desensitizing mammals against allergic reaction, in accordance with the invention, comprises administering to an atopic mammal, prior to or after exposure to an antigen, a dosage of a polypeptide fraction derived by proteolytic enzymatic digestion from a specific allergen causing said allergic reaction in an amount effective to inhibit significantly immunological reactions without inducing anaphylaxis in said mammal, said fraction consisting essentially of a degraded polypeptide having a molecular weight of less than about 10,000, and a nominal molecular radius not greater than about 15 angstroms.

All large polypeptide molecules including ragweed antigen, bee venom phospholipase A, and egg white ovalbumin are complex immunologic entities. They contain a large number of possible sites which are recognized as foreign by the host animal or human, and the immunologic response is to produce antibodies which will react with many of these epitopes. In order to obtain an immunologic response a minimum of two binding sites on the antigen are necessary. This same requirement for a minimum of two binding sites is also necessary for an allergic response, e.g. anaphylaxis. Thus there is a relationship between immunologic response and immunologic reactivity. The products of this invention are a series of polypeptide fractions which are assumed to have only one functional binding site on each molecule. Thus the epitopes on this molecule can only have partial recognition or reactivity. Although not wishing to be bound by theory, it is believed that it is this inability to form the complete reaction which confers the unique properties.

Polypeptide molecules, when degraded by proteolytic enzymes, form a series of products of varying molecular size. Short degradation times or very small amounts of enzyme degrade the molecule partially, yielding large fragments. In contrast, large amounts of enzyme or long digestion times result in more completely degraded polypeptide. The product of this invention results from the choice of the appropriate enzyme to form polypeptides which have the unique immunological properties. Too little degradation would result in polypeptides having properties similar to the native molecules, while too much degradation would result in fragments which have no immunologic or immunochemical reactivity. In the case of ragweed pollen it has been found that fragments having a molecular weight of less than about 2,000 have no immunologic or immunochemical reactivity.

Purification of the product may be needed to remove those allergenic molecules with too great an immunologic reactivity. This is accomplished by selecting polypeptide fragments having a molecular weight less than about 10,000 and a nominal molecular radius not greater than about 15 angstroms. If still present, strongly reacting polypeptides can be removed by affinity chromatography of allergen specific antibody columns.

It is within the scope of the invention to control carefully the digestion of the allergen by proteolytic enzymes in such manner that substantially no residual reactive antigens remain, thus making it unnecessary to carry out a purification or selection step by means of molecular exclusion chromatography, molecular filtration or affinity absorption. A purification or detoxification step in the present method is thus considered to be optional but preferred for safety.

DETAILED DESCRIPTION OF THE INVENTION

Preparation I

Short Ragweed Extract and Fraction A

Defatted short ragweed pollen, 10 g, was added to distilled water, 50 ml, and stirred for 48 hours at 4° C., or optionally as little as 2 hours at 25° C. The slurry was filtered through paper on a Buchner funnel, the filtrate being whole ragweed pollen aqueous extract. To this extract, solid ammonium sulfate was added to 90% saturation and the mixture was maintained for 2 to 3 hours at 4° C. and centrifuged. The precipitate was separated and dissolved in 3.5 ml of 0.1 M TRIS buffer and 0.06 HCL (pH 7.9). This buffered solution was run through a Sephadex G-25 polydextran molecular sieve column 95 cm high and 4 cm in diameter which had been equilibrated with 0.025 M TRIS and 0.015 M HCL (pH 7.9). The first peak raffinate from the column was fraction A. To assure purification, Fraction A was optionally again passed through the column. The raffinate was centrifuged and the supernatant portion was lyophilized.

EXAMPLE 1

Lyophylized Fraction A from Preparation I was dissolved in 0.1 M sodium bicarbonate buffer, pH 8.0, at a concentration of 20 mg/ml. Nagarase proteolytic enzyme from B subtilis was dissolved in 0.1 M sodium bicarbonate buffer, pH 8.0, to make a concentration of 20 mg/ml. The nagarase solution was added to the Fraction A solution to give a final ratio of Fraction A 100 parts to nagarase 1 part. After incubation for 24 hours at room temperature the enzyme digestion was stopped by the addition of PMSF stock solution, 190 mg per ml in 0.1 M sodium bicarbonate (pH 8.0), added to the enzyme digest to produce a molarity ratio of PMSF to nagarase of 1.5:1. This was the crude polypeptide active ragweed pollen immunizing fraction.

EXAMPLE 2

Lyophilized Fraction A from Preparation I was dissolved in 0.1 M citrate phosphate buffer, pH 3.0, at a concentration of 200 mg of Fraction A per 10 ml of buffer solution and repeatedly slowly passed through a column of immobilized pepsin enzyme on glass beads. After 20 passages at room temperature the digest was removed from the column and lyophilized.

EXAMPLE 3

A citrate-phosphate buffer (pH 3.0) was prepared from 39.8 ml of 0.1 M citric acid and 10.2 ml of 0.2 M dibasic sodium phosphate diluted to 100 ml with distilled water. The lyophilized Fraction A from Preparation 1 was dissolved in this buffer solution in a proportion of 20 mg of Fraction A per ml of buffer. To this was added an aliquot of 5 mg of pepsin in 1 ml of distilled water to give a ratio of Fraction A to pepsin of 100 to 1. The solution was maintained for 24 hours at room temperature and then brought to pH 7.4 by the addition of 0.1 M sodium hydroxide. The resulting product was the crude ragweed polypeptide active immunosuppressant fraction.

EXAMPLE 4

Bee venom phospholipase A, (Sigma Chemical Co., St. Louis, Mo. #P2509) 100 mg, was dissolved in citrate phosphate buffer, pH 3.0, 10 ml, and stirred for 1 hour at 25° C. The pH was adjusted to 3.0 by addition of 1 N HCl. Digestion was performed by adding 5 mg of pepsin (bovine) and the reaction was allowed to proceed for 6 hours at 25° C. The reaction was terminated by the addition of 1 N NaOH to bring the pH to 8.0. This destroyed any residual pepsin activity. The resulting product was the crude phospholipase A polypeptide active immunosuppressant fraction.

EXAMPLE 5

Ovalbumin (Sigma Chemical Co. Fraction V) 1 g was added to distilled water, 100 ml, and stirred for 1 hour at 25° C. The pH was adjusted to 3.0 by addition of 1 N HCl. Digestion was performed by adding 50 mg of pepsin (bovine) and the reaction was allowed to proceed for 6 hours at 25° C. The reaction was terminated by the addition of 1 N NaOH to bring the pH to 8.0. This destroyed any residual pepsin activity. The resultant product was the crude ovalbumin polypeptide active immunosuppressant fraction.

EXAMPLE 6

The products of Examples 1 through 5 were further purified by passing each of them through an affinity absorption column prepared as follows: Sepharose CL-4B polydextran was washed with distilled water. Sepharose CL-4B washed, 0.5 volume and distilled water 0.5 volume were added to 1 volume of 2 M sodium carbonate and stirred slowly. To this slurry, 0.5 volume of 2 g per ml of cyanogen bromide in acetonitrile was added all at once. The slurry was stirred vigorously for 2 minutes. The Sepharose was then washed with 10 volumes of 0.1 M sodium bicarbonate, pH 9.5. The slurry was filtered under vacuum and the filter cake was transferred to a flask containing 100 ml of 1 percent of a gamma globulin antibody to the specific allergen, for example human ragweed gamma globulin in 2 M sodium bicarbonate. Coupling of the Sepharose and globulin was effected by maintaining the preparation at 4° C. for 20 hours. After coupling, the Sepharose beads were washed successively with 20 volumes each of 0.1 M sodium acetate, pH 4.0, 0.1 M sodium bicarbonate, and physiological saline. Lowry determinations done before and after coupling demonstrated 86.3% efficiency of coupling of human gamma globulin to Sepharose beads.

The purified products of each of Examples 1 through 5 obtained in this Example have substantially identical biochemical and immunological properties. The resulting unabsorbed allergen digest, the polypeptide active immunosuppressive fraction, is used for the treatment of allergy. If desired, the raffinate may be lyophilized to produce a dry solid product which keeps well and may be resuspended in saline for therapeutic use.

The material prepared from ragweed pollen has a molecular weight of less than about 10,000 but not less than about 2,000. The antigenic determinants not absorbed out by antibodies are still retained.

EXAMPLE 7

The products of Examples 1 through 5 were further purified by passing each of them through a molecular sieve or gel filtration column prepared as follows:

Sepharose G-50, 500 g, was allowed to swell overnight in 2 liters of phosphate buffered saline, pH 7. The resulting slurry was stirred, allowed to settle and the fine particles decanted. A column of the material was made by adding the slurry carefully to a 10 cm × 200 cm glass column. The polypeptide fractions of ragweed, bee venom or ovalbumin respectively, eluted in the fraction of less than about 10,000 molecular weight.

EXAMPLE 8

The products of Examples 1 through 5 were further purified by passing each of them through a molecular sieve such as the Millipore immersible CX-10, Amicon PM-10, UM-10, UM-5. The fractions were purified by ultrafiltration either by vacuum or pressure. The filters did not allow passage of molecules greater than a nominal molecular radius of about 15 angstroms.

As an aid in interpreting the data of Tables I through XIII hereinafter, the following definitions are set forth:
(1) Non-immunogenic Substance: When administered by injection in the presence of an adjuvant, there is no or a very poor immune response. This is accomplished by one or several injections of the polypeptide fractions. Testing for the immune response is done by using the passive cutaneous anaphylaxis (PCA) reaction.
(2) Non-antigenic Substance: When administered to an animal sensitized by antibodies to the specific antigen, the polypeptide fraction causes no allergic reaction. This is accomplished by injecting antibody subdermally where it adheres to host mast cells followed by a challenge with the antigen. This treatment normally results in a passive cutaneous anaphylaxis (PCA) reaction. No reaction indicates loss of antigenicity.
(3) Immunosuppressive Substance: When administered prior to or after the antigen, the polypeptide fraction reduces or eliminates the allergic response. Thus treatment with the polypeptide fraction lowers or eliminates the expected or ongoing IgE response as tested by PCA.
(4) Passive Cutaneous Anaphylaxis (PCA): A highly sensitive and reliable test of immediate hypersensitivity based on measuring titers of antibodies that sensitize mast cells and basophils. PCA is equivalent to PK reaction in humans.
(5)
Primary Response: Following first exposure to the antigen.
Secondary response: Following second or multiple exposures to antigen.

The tests reported in Tables I through XIII are averages based on either two or three experiments.

EXAMPLE 9

BDF$_1$ mice were injected intraperitoneally with ragweed extract and alum as an adjuvant. Immune response was measured by passive cutaneous anaphylaxis (PCA) reaction in rat skin. The PCA challenge consisted of 1 mg ragweed extract dissolved in 1 ml of 1%

Evans blue. Polypeptide active pollen immunosuppressive fraction (PAPIF) was also injected, with results summarized in Table I.

TABLE I
IMMUNOGENIC PROPERTIES OF PAPIF

| Preparation** | Primary Response at 10 days PCA Titer | Secondary Response at 40 days* PCA Titer |
|---|---|---|
| Ragweed Ext. 10 μg | 1:320 dilution | 1:1620 dilution |
| Ragweed Ext. 100 μg | 1:160 dilution | 1:1620 dilution |
| PAPIF 10 μg | 0 | 0 |
| PAPIF 100 μg | 0 | 0 |

Titer represents mean of sera pooled from 5 mice
*Second injection was given at 30 days
**Dose i.p. in alum.

The above data show complete lack of immunogenicity of PAPIF in both primary and secondary immune responses are compared with ragweed extract which effected responses at dilutions of 1:160 and 1:1620.

EXAMPLE 10

To test the effect of ragweed PAPIF as an immunosuppressant, mice were injected I.V with PAPIF of Examples 3 and 6 prior to immunization with ragweed extract in accordance with Table II.

TABLE II
IMMUNOSUPPRESSIVE PROPERTIES OF PAPIF

| Pretreatment with PAPIF* | Challenge with Ragweed Ext.** | PCA Titer Day 10 |
|---|---|---|
| 100 μg day 0 | 100 μg day 1 | 0 |
| 10 μg day 0 | " | 0 |
| 1 μg day 0 | " | 1:10 |
| 100 μg day 1 | " | 1:10 |
| 10 μg day 1 | " | 1:20 |
| 1 μg day 1 | " | 1:40 |
| 0 | " | 1:160 |

Titer represent mean of sera pooled from 5 animals
*i.v. adm. in saline
**i.p. in alum.

The data of Table II clearly show the immunosuppressive effect of PAPIF on the immune response to ragweed antigen in the primary immune response.

A similar degree of suppression by I.V. injection of the product of Examples 2 and 6 was observed during the secondary immune response to ragweed antigen in accordance with Table III.

TABLE III
IMMUNOSUPPRESSIVE PROPERTIES OF PAPIF IN SECONDARY RESPONSE

| Pretreatment with PAPIF* | Challenge with Ragweed Ext.** | PCA day 40 |
|---|---|---|
| 100 μg day 0, day 29 | 100 μg day 1, day 30 | 1:10 |
| 10 μg day 0, day 29 | " | 1:40 |
| 1 μg day 0, day 29 | " | 1:80 |
| 0 | " | 1:3200 |

Titer represents mean of sera pooled from 5 animals
*i.v. in saline
**i.p. in alum.

The effects of PAPIF prepared in accordance with Example 2 in the inhibition of ongoing immune response to ragweed antigen was also demonstrated. After IgE response became evident the animals were injected I.V. with PAPIF in accordance with Table IV.

TABLE IV
EFFECT OF PAPIF ON ONGOING RESPONSE

| Treatment With PAPIF on Day 6, 7, 8* | Treatment With Ragweed Ext. on Day 1** | PCA Day 20 |
|---|---|---|
| — | 100 μg | 1:160 |
| 100 μg | 100 μg | 1:10 |
| 100 μg | — | 0 |

Titer represents mean of sera pooled from 5 animals
*i.v. in saline
**i.p. in alum.

Thus administration of PAPIF was suppressive even to ongoing IgE response.

EXAMPLE 11

The PAPIF material of Example 8 was tested in humans either non-sensitive or sensitive specifically to ragweed antigen.

Fraction A and purified PAPIF were prepared at a concentration of 1 mg per ml in non-pyrogenic saline and filtered through a 0.25μ Millipore bacterial filter. The filtrate was further diluted with sterile isotonic saline to $10^{-3}$ to $10^{-6}$ dilutions and skin reactivity tested to intradermal injection of 0.02 ml per injection as follows:

In three non-atopic individuals, the $10^{-3}$ to $10^{-6}$ dilutions caused no skin reaction. This shows PAPIF at these concentrations to have no inherent reactivity in normal individuals.

In three atopic individuals, the following reactions were observed with the intensity of wheal graded from a maximum of plus four down to zero as reported in Table V. These data demonstrate that PAPIF was almost non-reactive even in the most concentrated solution tested in atopic individuals.

TABLE V
REACTIVITY OF PAPIF IN RAGWEED SENSITIVE PATIENTS

| Dilution of Preparat.* | Patient A | | Patient B | | Patient C | |
|---|---|---|---|---|---|---|
| | Fraction A | PAPIF | Fraction A | PAPIF | Fraction A | PAPIF |
| $10^{-3}$ | ++++ | +,0 | ++++ | 0 | ++++ | +,0 |
| $10^{-4}$ | ++++ | 0 | ++ | 0 | ++++ | 0 |
| $10^{-5}$ | ++ | 0 | ++ | 0 | +++ | 0 |
| $10^{-6}$ | + | 0 | + | 0 | ++ | 0 |

*Undiluted preparation contained 1 mg/ml of the fraction.

EXAMPLE 12

Table VI demonstrates blocking activity of PAPIF in rats intradermally sensitized with reaginic IgE anti ragweed antibodies prepared in $BDF_1$ mice. PAPIF was administered I.V. 15 min. prior to I.V. challenge with Fraction A and Evans Blue. As shown, Table VI PAPIF substantially reduced reactivity between IgE antibody and antigen.

TABLE VI
BLOCKING ACTIVITY OF PAPIF

| Anti Ragweed IgE Serum Dilution | PCA | |
|---|---|---|
| | No PAPIF* | PAPIF |
| 1:10 | +++ | +++ |
| 1:20 | +++ | +++ |
| 1:40 | +++ | +++ |
| 1:80 | +++ | + |
| 1:160 | +++ | — |

TABLE VI-continued

BLOCKING ACTIVITY OF PAPIF

| Anti Ragweed | PCA | |
|---|---|---|
| IgE Serum Dilution | No PAPIF* | PAPIF |
| 1:320 | + | − |
| 1:640 | − | − |

*Fraction A 100 μg in 1.0 Ml 0.5% Evans Blue given I.V. 15 min. after PAPIF

EXAMPLE 13

Table VII demonstrates that fragments having molecular weight less than 10,000 are not reactive in PCA challenge.

Rats were sensitized intradermally with anti ragweed IgE antibodies prepared in $BDF_1$ mice. 24 hours later they were challenged I.V. with 1 mg of the appropriate fragments purified by ultrafiltration (Example 8) in 1 ml 0.5% Evans Blue. It is evident that fragments having a molecular weight less than 10,000 were not reactive in PCA.

TABLE VII

PCA REACTIVITY OF FRAGMENTS

| Approximate Molecular Weight of Fragments | PCA* |
|---|---|
| 20,000–30,000 | +++ |
| 10,000–20,000 | +++ |
| 2,000–10,000 | − |
| <2,000 | − |
| − | − |

*Sensitizing antiserum 1:50 dilution

EXAMPLE 14

The immunosuppressant activity of the fragments separated by ultrafiltration (see Example 8) is shown in Table VIII.

The fragments were administered I.V. to groups of $BDF_1$ mice which were subsequently immunized with Fraction A in alum. Fragments having a molecular weight less than 2,000 were found not to be immunosuppressive.

TABLE VIII

| Approx. Molecular Weight of Fragmts. | Pretreatment | Challenged With Ragweed** | PCA |
|---|---|---|---|
| 20,000–30,000 | 10 μg (3X) | 100 μg | 1:5 |
| 10,000–20,000 | 10 μg (3X) | 100 μg | 1:10 |
| 2,000–10,000 | 10 μg (3X) | 100 μg | 1:10 |
| <2,000 | 10 μg (3X) | 100 μg | 1:320 |
| − | − | 100 μg | 1:320 |

*Mice pretreated by intravenous injection 24, 48 and 72 hours before challenge with ragweed
**In 1 mg of alum injected intraperitoneally

EXAMPLE 15

The immunogenic, immunosuppressive and antigenic properties of phospholipase A fragments (Fr 1) are demonstrated in Tables IX, X and XI. The properties of these fragments are identical to those of PAPIF described in Examples 9 and 10.

TABLE IX

IMMUNOGENICITY OF PHOSPHOLIPASE FRAGMENTS

| Preparation* | 14 d. PCA | 21 d. PCA |
|---|---|---|
| PS A** | 160 | 320 |
| PS A | 320 | 640 |
| Fr. 1*** | 0 | 0 |

*Administered i.p. in alum.
**phospholipase A
***Fragment 1
Titer represents mean from 5 pooled sera.

TABLE X

SUPPRESSION BY PHOSPHOLIPASE FRAGMENTS

| Pretreatment* | Immunization** | 21 d. PCA |
|---|---|---|
| Fr. 1 10 μg (3X) | PS 10 μg | 0 |
| Fr. 1 10 μg (3X) | — | 0 |
| — | PS 10 μg | 640 |

*i.v. in saline
**i.p. in alum.
Titers means from 5 pooled sera.

TABLE XI

ANTIGENICITY OF PHOSPHOLIPASE FRAGMENTS

| Sensitiz. With* | Challenge | PCA |
|---|---|---|
| Anti Ps IgE | PS 100 μg | 160 |
| Anti PS IgE | Fr 1 100 μg | 0 |
| Anti PS IgE | Saline | 0 |

*Antibody injected intradermally 24 hours prior to i.v. challenge with antigen dissolved in 10 ml of .5% Evans blue dye.

EXAMPLE 16

The phospholipase A fragments (Fr 1) of Examples 4 and 6 were tested in humans non-sensitive or sensitive to bee venom. Table XII shows results of testing which demonstrate that Fr 1 is non-reactive in bee venom sensitive patients at concentration of 1 μg.

TABLE XII

SKIN TESTING OF BEE VENOM SENSITIVE PATIENTS

| | Reaction | | |
|---|---|---|---|
| Test Material | Patient #1 | Patient #2 | Patient #3 |
| Bee venom 1 μg | ++++ | −+ | 0 |
| Phospholipase 1 μg | ++++ | −++ | 0 |
| Fraction 1 1 μg | 0 | 0 | 0 |
| Saline | 0 | 0 | 0 |

EXAMPLE 17

Ovalbumin fragments (OVA Fr) prepared as described in Example 5 were tested for their immunogenic, suppressive and antigenic properties. The properties of these fragments were identical to those of PAPIF and phospholipase A fragments as described in Examples 9, 10 and 15.

Table XIII shows immunosuppressive properties of OVA fragments in $BDF_1$ mice.

TABLE XIII

SUPPRESSION BY OVA FRAGMENTS

| Pretreatment* | Immunization** | 21 d. PCA |
|---|---|---|
| OVA Fr. 10 μg (3x) | OVA 10 μg | 0 |
| OVA Fr. 10 μg (3x) | — | 0 |
| — | OVA 10 μg | 320 |

*i.v. in saline
**i.p. in alum
Titers means from 5 pooled sera

By way of summary, Table I discloses that the fragments were quite non-immunogenic even when administered in an adjuvant.

Immunosuppressive activity of these fragments is documented in Tables II, III and IV. These data show that the fragments were effective when administered prior to primary or secondary response or even after the response was ongoing.

Table V shows that ragweed fragments were quite non-reactive in ragweed sensitive patients when administered intradermally.

Tables VI to VIII demonstrate the blocking, and molecular weight dependency of the properties of the ragweed fragments.

Tables IX to XI demonstrate properties of fragments (Fr1) prepared from phospholipase A (PSA), the major component of bee venom in accordance with Examples 4 and 6. These tables clearly show that phospholipase A fragments were effective immunosuppressants.

Table XII shows that phospholipase A fragments were quite non-reactive in individuals sensitive to bee venom.

Table XIII shows results of experiments in which hen albumin (OVA) and its fragments (Fr OVA) prepared in accordance with Examples 5 and 6 were administered prior to parenteral challenge with OVA in alum. A high degree of suppression was achieved.

The above test data demonstrate that the polypeptide fractions of the present invention have lost the ability to cause allergic reaction, i.e. release of vasoactive amines from antibody-sensitized mast cells and basophils. However, the polypeptide fractions retain their immunoregulatory properties, and administration of the product of the invention to experimental animals parenterally inhibits initiation or continuation of ongoing IgE immune response to the specific allergen being treated.

In a typical case of pollen or ragweed allergy, desensitization is accomplished by treating the patient biweekly with the appropriate fragments. Since these fragments are relatively non-exacerbating, relatively large doses of it can be injected subcutaneously to achieve fast desensitization safely. For example, injection of 0.1 ml of $10^{-3}$ dilution of PAPIF (basic solution containing 1 mg of PAPIF per ml) is instituted biweekly for several weeks, desirably within three months prior to the beginning of the patient's ragweed sensitivity season. At the same time, the patient is tested by radioimmunoassay for concentration of specific antiragweed IgE as well as for the skin reactivity to ragweed antigen. As a result of desensitization there is no increase in levels of antiragweed IgE upon exposure of the individual to the ragweed. In addition, the reactivity of the desensitized individual to ragweed extract is significantly reduced.

The present invention represents an advance in two areas from the standpoint of processing and ease of administration. First, it has been found that digestion of an allergen by proteolytic enzymes can be controlled to such a degree that it is not necessary to remove residual reactive antigens. Thus the step of controlled enzymatic digestion of the allergen results in the desired final product. Second, it has been found that parenteral administration of the product to mice in relatively large doses results in suppression of the IgE immune response.

We claim:

1. An allergen desensitizing polypeptide fraction derived by proteolytic enzymatic digestion from a specific globular protein allergen causing the allergic reaction to be treated, said allergen being a native pollen or insect venom containing phospholipase A, said fraction consisting essentially of a degraded polypeptide having a molecular weight of less than about 10,000, a nominal molecular radius not greater than about 15 angstroms, an inability to precipitate with specific antibodies, an inability to induce substantial passive cutaneous anaphylaxis reaction in a sensitized mammal, an inability to release histamine from sensitized mast cells or basophils, an inability to induce substantial antibody response, and a capability of inducing antigen-specific suppression.

2. The allergen desensitizing polypeptide fraction claimed in claim 1, wherein said native pollen is ragweed pollen, and wherein the molecular weight of said fraction is not less than about 2,000.

3. A method of producing an allergen desensitizing polypeptide fraction which comprises subjecting an aqueous extract of a native globular protein allergen to digestion by a proteolytic enzyme, said allergen being a native pollen or insect venom containing phospholipase A, controlling the digestion time and conditions and separating residual reactive product after said proteolytic digestion, thereby obtaining a final reaction product consisting essentially of a degraded polypeptide fraction having a molecular weight of less than about 10,000 and a nominal molecular radius not greater than about 15 angstroms, said degraded polypeptide fraction exhibiting an inability to precipitate with specific antibodies, an inability to induce substantial passive cutaneous anaphylaxis in a sensitized mammal, an inability to induce substantial antibody response, and a capability of inducing antigen-specific suppression.

4. The method claimed in claim 3, wherein said enzyme is carboxypeptidase A, trypsin, chymotrypsin, papain, bacterial protease, nagarase, or pepsin.

5. The method claimed in claim 3, wherein said step of separating residual reactive allergen comprises detoxifying said reaction product by molecular exclusion chromatography, molecular filtration, or affinity absorption of said residual reactive antigens.

6. The method claimed in claim 3, wherein said allergen is ragweed pollen and said enzyme is nagarase or pepsin.

7. The method claimed in claim 3, wherein said allergen is insect venom phospholipase A and said enzyme is pepsin.

8. A method of desensitizing a mammal against allergic reaction, which comprises administering to an atopic mammal, prior to or after exposure to an antigen, a dosage of a polypeptide fraction derived by proteolytic enzymatic digestion from a specific globular protein allergen causing said allergic reaction in an amount effective to inhibit significantly immunological reactions without inducing anaphylaxis in said mammal, said allergen being a native pollen or insect venom containing phospholipase A, said fraction consisting essentially of a degraded polypeptide having a molecular weight of less than about 10,000, and a nominal molecular radius not greater than about 15 angstroms.

9. The method claimed in claim 8, wherein said specific globular protein allergen is insect venom containing phospholipase A.

10. The method claimed in claim 9, wherein said specific allergen is ragweed pollen.

11. The method claimed in claim 8, wherein said polypeptide fraction is administered parenterally.

12. The method claimed in claim 8, which comprises administering to an atopic mammal the polypeptide fraction of claim 1.

13. The allergen desensitizing polypeptide fraction claimed in claim 1, wherein said specific allergen is insect venom containing phospholiphase A.

* * * * *